United States Patent
Ojima et al.

(10) Patent No.: US 8,110,250 B2
(45) Date of Patent: Feb. 7, 2012

(54) METHOD FOR FABRICATING CHEMICAL SENSOR ELEMENT

(75) Inventors: Tetsunori Ojima, Kawasaki (JP); Miki Ogawa, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 13/033,198

(22) Filed: Feb. 23, 2011

(65) Prior Publication Data
US 2011/0143026 A1 Jun. 16, 2011

Related U.S. Application Data

(62) Division of application No. 11/745,062, filed on May 7, 2007, now abandoned.

(30) Foreign Application Priority Data

May 12, 2006 (JP) ................................. 2006-134095

(51) Int. Cl.
*B05D 5/06* (2006.01)
(52) U.S. Cl. .................. 427/201; 427/430.1; 427/385.5; 427/537; 422/57; 436/8; 436/73; 436/80
(58) Field of Classification Search ............. 422/57; 436/8, 73, 80; 427/201, 430.1, 385.5, 537
See application file for complete search history.

(56) References Cited

U.S. PATENT DOCUMENTS

| | | | |
|---|---|---|---|
| 3,634,135 A | 1/1972 | Akiyama et al. | |
| 3,846,345 A | 11/1974 | Mason et al. | |
| 3,956,662 A | 5/1976 | McTeague et al. | |
| 4,039,896 A | 8/1977 | McTeague et al. | |
| 4,106,937 A | 8/1978 | McTeague et al. | |
| 4,131,821 A | 12/1978 | Mossman | |
| 4,940,959 A | 7/1990 | Zeller et al. | |
| 4,976,831 A * | 12/1990 | Murrer et al. | 205/533 |
| 5,322,751 A | 6/1994 | Chou et al. | |
| 5,607,643 A | 3/1997 | Xiaoming et al. | |
| 6,891,322 B2 | 5/2005 | Lee et al. | |
| 2002/0135291 A1 | 9/2002 | Taniguchi et al. | |
| 2002/0140339 A1 | 10/2002 | Lee et al. | |
| 2003/0068446 A1* | 4/2003 | Mirkin et al. | 427/430.1 |
| 2004/0053354 A1 | 3/2004 | Ikawa et al. | |
| 2005/0130324 A1 | 6/2005 | West et al. | |
| 2006/0012282 A1 | 1/2006 | Nanataki | |
| 2008/0117423 A1 | 5/2008 | Ogawa et al. | |

FOREIGN PATENT DOCUMENTS

| | | |
|---|---|---|
| JP | 7-12716 A | 1/1995 |
| JP | 2002-365210 A | 12/2002 |
| JP | 3452837 B | 7/2003 |
| JP | 2003-329682 A | 11/2003 |

OTHER PUBLICATIONS

Translation of JP 2000-356587 (Corresponds to JP 3452837 B).

* cited by examiner

*Primary Examiner* — Brian R Gordon
*Assistant Examiner* — Shogo Sasaki
(74) *Attorney, Agent, or Firm* — Fitzpatrick, Cella, Harper & Scinto

(57) ABSTRACT

A chemical sensor that utilizes localized surface Plasmon resonance including a substrate, metal-containing particles and dielectric particles, wherein the metal-containing particles and the dielectric particles are disposed on the substrate, is used as a chemical sensor element. Thereby, a chemical sensor element having a sufficient detecting sensitivity when localized surface Plasmon resonance is utilized, and a method for the fabrication thereof, can be provided.

3 Claims, 3 Drawing Sheets

METHOD FOR FABRICATING CHEMICAL SENSOR ELEMENT

CROSS-REFERENCE TO RELATED APPLICATIONS

This application is a division of application Ser. No. 11/745,062, filed May 7, 2007, now abandoned, which claims the benefit of Japanese Patent Application No. 2006-134095, filed May 12, 2006. All prior applications are incorporated herein by reference in their entireties.

BACKGROUND OF THE INVENTION

1. Field of the Invention

The present invention relates to a chemical sensor element and a method for fabricating the same.

2. Description of the Related Art

Heretofore, methods for measuring a change between before and after the antigen-antibody reaction of an antibody or an antigen adsorbed on fine metal particles with the antigen or the antibody by utilizing localized surface Plasmon resonance have been known. For example, U.S. Pat. No. 5,607,643 discloses a method for detecting localized surface Plasmon resonance by a Raman spectrum and Raman scattering intensity. By this method, an antigen of a substance to be measured is added to the surfaces of fine metal particles on which an antibody has been previously adsorbed to cause an antigen-antibody reaction and form an immune complex. The formed immune complex can be identified from the Raman spectrum in this state. Further, it is disclosed that the added objective substance can be quantitatively determined from Raman scattering intensity on the surface of fine metal particles adsorbing the immune complex.

A biosensor that can be applied to the present invention is a measuring device utilizing an excellent biological molecular recognizing ability of living organisms or biological molecules. It has wide applications not only in the medical fields, but is also expected to be applicable in the environmental or food areas.

In general, a biosensor includes a capturing substance to recognize and capture a substance to be measured (hereafter referred to as "target substance"), and a detecting element to detect physical and chemical change that occurred at the time and convert the change to a signal that can be detected, such as an electrical signal and an optical signal. In living organisms, there are combinations of substances with affinity for each other, such as enzyme-substrate, antigen-antibody and DNA-DNA. The biosensor utilizes the principle wherein a component of these combinations can be selectively measured by disposing the other component on or in a base material to use as a capturing substance component. As the detecting element, various systems, such as an oxygen electrode, a hydrogen peroxide electrode, an ion electrode, ISFET and a thermistor are proposed. Recently, a quartz oscillator, an SAW element or the like that can detect a change in mass on a nanogram scale, may be used.

The measuring method utilizing localized surface Plasmon resonance employs a simple configuration of the assay because labeling molecules, for example with a fluorescent colorant, is not required; and the process of an adsorbing reaction onto the surfaces of fine metal particles can be directly monitored in real time. Therefore, the application of the measuring method utilizing localized surface Plasmon resonance to various assays is expected. An example of such an application is an affinity assay, such as an immunoassay utilizing the specificity of the antigen-antibody reaction.

Japanese Patent No. 3,452,837 (Japanese Patent Application Laid-Open No. 2000-356587) discloses, as a sensor element that can be effectively used in affinity assay, a localized surface Plasmon resonance sensor wherein a plurality of fine metal particles are fixed on a substrate, and the refractive index of the medium using the Plasmon resonance of the fine metal particles is determined.

However, in a sensor element of the configuration wherein fine metal particles are fixed on a substrate utilizing localized surface Plasmon resonance, fine metal-containing particles may be aggregated, or may be disposed on the substrate at an extremely uneven density, during cleaning or drying in the process of fabricating the sensor element. In addition, fine metal-containing particles may also aggregate during cleaning or drying in an assay detection using the above-described sensor element. As a result, the detection sensitivity of the sensor may be extremely reduced. Specifically, aggregation of metal-containing particles is a big problem in the face of expanding the application of the measuring method utilizing localized surface Plasmon resonance.

Furthermore, there is a tendency for the metal-containing particles to become aggregated easier if their concentration is elevated. Consequently, the disposition of metal-containing particles on the substrate at a high density may become difficult.

SUMMARY OF THE INVENTION

To solve the above-described problems, an object of the present invention is to provide a chemical sensor element that can achieve sufficient detection sensitivity by utilizing localized surface Plasmon resonance, and a method for fabricating such a chemical sensor element.

The present invention is directed to a chemical sensor element for determining a property of a liquid specimen comprising:

a substrate, metal-containing particles and dielectric particles, wherein the metal-containing particles and the dielectric particles are disposed on the substrate.

The diameter of the metal-containing particles can be in the range of 1 nm to 1000 nm, and the diameter of the dielectric particles is in the range of 1 nm to 1000 nm.

In the chemical sensor element for detecting target substances in the specimen, a target-capturing substance can be disposed in the metal-containing particles.

The present invention is directed to a method for fabricating a chemical sensor element wherein metal-containing particles are fixed on a substrate, comprising the steps of:

preparing a dispersion comprised of metal-containing particles and dielectric particles as the dispersoids;

contacting the dispersion with the substrate to fix the metal-containing particles and the dielectric particles on the substrate; and isolating the metal-containing particles and the dielectric particles fixed on the substrate from the dispersion.

The method for fabricating a chemical sensor element can further comprise the step of removing the dielectric particles fixed on the substrate.

According to the present invention, by mixing metal-containing particles with dielectric particles and fixing the particles on a substrate, the aggregation of the metal-containing particles with each other is reduced, and the metal-containing particles can be disposed on the substrate in the state wherein the metal-containing particles are at a uniform density. As a result, the chemical sensor element according to the present invention can achieve sufficient detection sensitivity.

Further features of the present invention will become apparent from the following description of exemplary embodiments with reference to the attached drawings.

DESCRIPTION OF THE EMBODIMENTS

Aspects included in the present invention will be described below in detail.

Configuration of Chemical Sensor Element

A chemical sensor element according to the present invention includes a substrate, metal-containing particles and dielectric particles, and these two kinds of particles are disposed on the substrate. The metal-containing particles are preferably disposed on the substrate at a uniform density.

The chemical sensor element can determine the properties of a liquid specimen by using a localized surface Plasmon resonance method. The properties of the liquid specimen are determined by measuring the refractive index around the metal-containing particles fixed to the chemical sensor element. Therefore, if a sensor element, wherein a substance with particular affinity for a specific substance (target substance) (target-capturing substance) is fixed to the metal-containing particles, is used, the specific substance (target substance) contained in a liquid specimen is held on the surfaces of the metal-containing particles, causing the refractive index of the surfaces of the metal-containing particles to change. In other words, the chemical sensor element according to the present invention can be favorably used for the detection of a specific substance (target substance) contained in a liquid specimen.

The diameter of a metal-containing particle can be selected within a range where localized surface Plasmon resonance is caused, and metal-containing particles can be dispersed in the dispersion. The diameter is preferably not less than 1 nm and not more than 1000 nm.

Examples of the metals contained in the metal-containing particles include gold, silver, copper, aluminum, and an alloy having two or more such metals. The metal-containing particles can contain one or more of these metals. Particles having these metals cause localized surface Plasmon resonance. Other than these metals, the metal-containing particles can also contain inorganic materials, such as silica, or organic materials, such as polystyrene.

The diameter of a dielectric particle can be selected within a range where dielectric particles can be dispersed in the dispersion. The diameter is preferably not less than 1 nm and not more than 1000 nm.

The materials utilized in the dielectric particles can be selected from any nonconductive materials, such as silica, polystyrene, and PMMA (polymethyl methacrylate).

Figure 1:
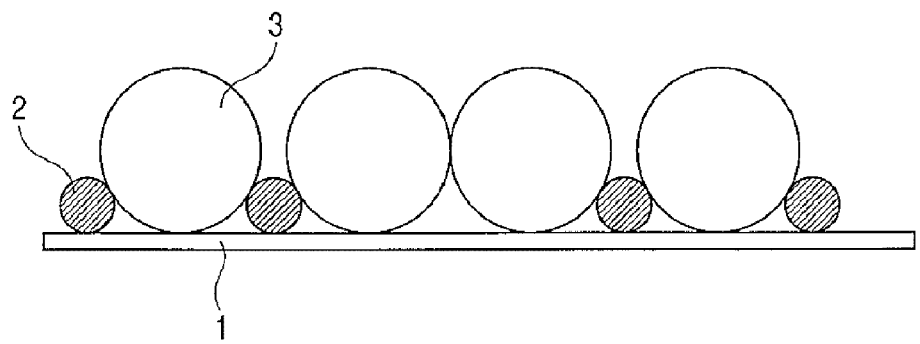
FIG. 1 is a schematic diagram illustrating an example of the chemical sensor element according to an embodiment of the present invention.

The diameter of a metal-containing particle can be different from the diameter of a dielectric particle. Specifically, the diameter of a dielectric particle can be larger than the diameter of a metal-containing particle as shown in FIG. 1. By the presence of dielectric particles, the aggregation of metal-containing particles can be prevented when the dispersion of the particles is removed.

Figure 2:
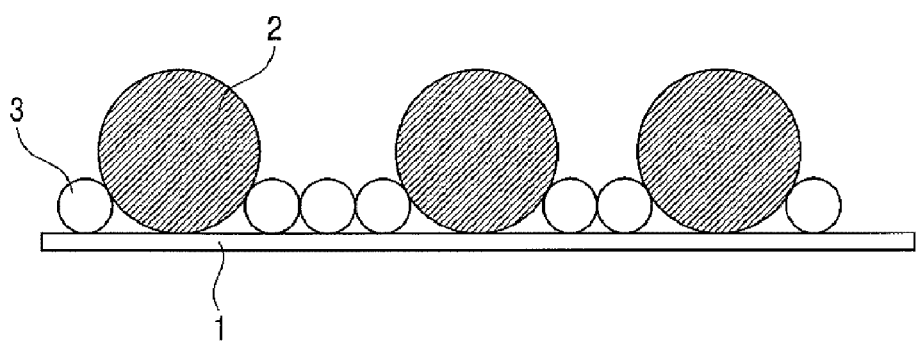
FIG. 2 is a schematic diagram illustrating another example of the chemical sensor element according to an embodiment of the present invention.

The diameter of a dielectric particle can also be smaller than the diameter of a metal-containing particle as shown in FIG. 2. In this case, molecules contained in a liquid specimen can easily contact the metal-containing particles.

When use in a chemical sensor element is considered, the diameters of metal-containing particles and dielectric particles are preferably not less than 1 nm. Furthermore, for easily dispersing the metal-containing particles and the dielectric particles, their diameters are preferably not more than 1000 nm.

As the material for the substrate 1, optically transparent glass, quartz, or plastics, such as polycarbonate and polystyrene, can be used. Specifically, the materials that enable the detection using a localized Plasmon resonance method can be used.

It is preferable for the absorbance of an optically transparent substrate at the wavelength used in measurement to be not more than 30%.

The surface of the substrate 1 can be modified by a functional group so as to elevate the affinity for metal-containing particles 2, or to form covalent bonds with chemically modified functional groups on the surfaces of metal-containing particles 2 and dielectric particles 3. Examples of functional groups that can be used to modify the surface of the substrate include amino, thiol and carboxyl groups.

When a chemical sensor element according to the present invention is used for the detection of a target substance, a chemical sensor element having a target-capturing substance with differential affinity for a target substance and a configuration wherein the target-capturing substance is fixed on the surfaces of metal-containing particles can be favorably used.

Method for Fabricating Chemical Sensor Element

A method for a fabricating chemical sensor element of the above-described configuration is described below.

A method for a fabricating chemical sensor element according to the present invention includes preparing a dispersion by dispersing metal-containing particles and dielectric particles, fixing the metal-containing particles and the dielectric particles on the substrate by allowing the dispersion to contact the substrate, and isolating the metal-containing particles and the dielectric particles fixed on the substrate from the dispersion.

As a dispersion medium for dispersing metal-containing particles and dielectric particles, water can be favorably used. An organic solvent, such as DMF (dimethyl formamide), can also be used as a dispersion medium.

Both of the two kinds of particles must be uniformly dispersed in the dispersion. In order to disperse metal-containing particles in the dispersion, the diameter of a metal-containing particle is preferably not less than 1 nm and not more than 1000 nm. In order to disperse dielectric particles in the dispersion, the diameter of a dielectric particle is preferably not less than 1 nm and not more than 1000 nm. In order to disperse the two kinds of particles in the dispersion, a surface active agent or the like can be added in the dispersion or the pH can be adjusted. An example of the surface active agents is Tween 20. When the surfaces of metal-containing particles include gold, citric acid can be favorably used as a component to accelerate the dispersion process.

In the dispersion before disposing metal-containing particles on the substrate, the metal-containing particles should be in a dispersed state.

Figure 3:
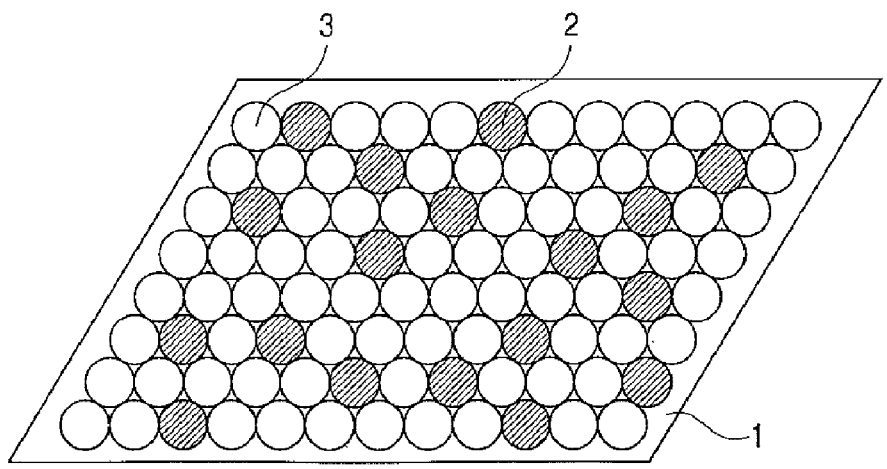
FIG. 3 is a schematic diagram illustrating another example of the chemical sensor element according to an embodiment of the present invention.
Figure 4:
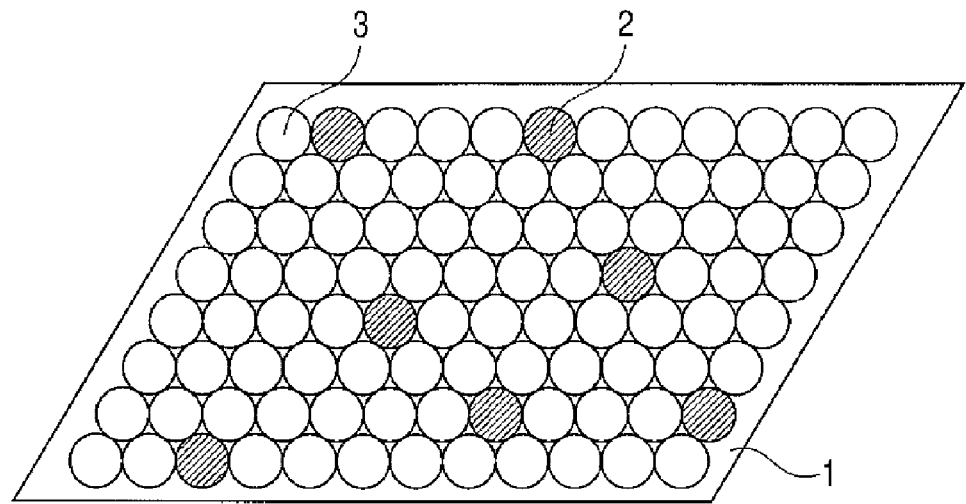
FIG. 4 is a schematic diagram illustrating still another example of the chemical sensor element according to an embodiment of the present invention.

The disposing density of the metal-containing particles on the substrate can be adjusted by the concentration of the metal-containing particles or the dielectric particles in the dispersion. The disposing density of the metal-containing particles on the substrate can be reduced, for example, by decreasing the concentration of the metal-containing particles, by elevating the concentration of the dielectric particles, or both, in the dispersion. Alternatively, the disposing density of the metal-containing particles on the substrate can be elevated by increasing the concentration of the metal-containing particles, by decreasing the concentration of the dielectric particles, or both, in the dispersion. Thereby, the disposing density of the metal-containing particles on the substrate can be controlled from the case when the disposing density is high, as shown in FIG. 3, to the case when the disposing density is low, as shown in FIG. 4. By thus controlling the disposing density, the detecting sensitivity of the chemical sensor element can be improved.

The isolation of the metal-containing particles and the dielectric particles fixed on the substrate from the substrate means to break the contact between the dispersion and the substrate by operations, such as the removal of the substrate from the dispersion and the removal of the dispersion from the container to make the dispersion contact the substrate.

The substrate isolated from the dispersion is properly cleaned and dried.

The method for fabricating the chemical sensor element according to the present invention can further include fixing metal-containing particles and dielectric particles on the substrate by the above-described fabricating method, and removing the dielectric particles fixed on the substrate. As the method for removing the dielectric particles, plasma ashing can be favorably used, but the method is not limited to plasma ashing. Examples of the materials for dielectric particles that can be decomposed by plasma ashing include organic materials, such as polystyrene.

The method for fixing a target-capturing substance to metal-containing particles can be any method as long as the capturing capacity of the target-capturing substance is not impaired. For example, when the target-capturing substance has a functional group with a high affinity for metals, such as thiol, disulfide and amino groups, the target-capturing substance can be directly fixed. Alternately, the target-capturing substance can be fixed via a coupling agent. For example, when the surface of a metal-containing particle is gold, and the target-capturing substance has a functional group with affinity for amino groups, aminoethanethiol, which has an amino group and a thiol group on both ends, can be used.

EXAMPLES

The present invention will be further specifically described below referring to examples. However, the present invention is not limited only to the following examples.

Example 1

Amino-group-modified polystyrene (manufactured by Sumitomo Bakelite Co., Ltd.) is used as a substrate; fine gold particles having a diameter of 100 nm (manufactured by BBI) are used as metal-containing particles; and carboxyl-group-modified polystyrene beads having a diameter of 100 nm (manufactured by Techno Chemical Corp.) are used as dielectric particles.

A dispersion of fine gold particles ($5.6 \times 10^9$ particles/ml) and polystyrene beads ($5.6 \times 10^9$ beads/ml) dispersed in pure water is prepared. A substrate is immersed in the dispersion and allowed to stand for 24 hours to dispose the fine particles on the substrate. After disposing, the substrate is cleaned with pure water, and dried by blowing nitrogen. The product is used as a chemical sensor element. A chemical sensor element can also be fabricated when the concentration of fine gold particles is changed within a range between $5.6 \times 10^8$ particles/ml and $5.6 \times 10^9$ particles/ml, and the concentration of polystyrene beads is changed within a range between $5.6 \times 10^8$ particles/ml and $5.6 \times 10^9$ particles/ml.

Example 2

Amino-group-modified quartz glass 4 (manufactured by Shin-Etsu Chemical Co., Ltd.) is used as a substrate; fine gold particles 5 having a diameter of 100 nm (manufactured by BBI) are used as metal-containing particles; and carboxyl-group-modified polystyrene beads having a diameter of 100 nm (manufactured by Techno Chemical Corp.) are used as dielectric particles.

Figure 5:
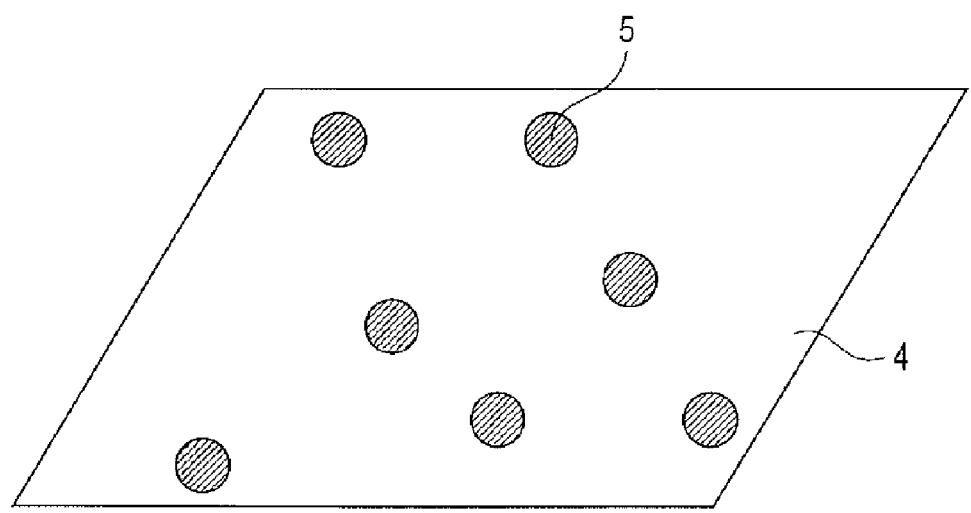
FIG. 5 is a schematic diagram illustrating the chemical sensor element of Example 2.

A dispersion of fine gold particles ($5.6 \times 10^9$ particles/ml) and polystyrene beads ($5.6 \times 10^9$ beads/ml) is prepared with pure water. A substrate is immersed in the dispersion and allowed to stand for 24 hours to dispose the particles on the substrate. After disposing, the substrate is cleaned with pure water, and dried by blowing nitrogen. After drying, the polystyrene beads are removed by plasma ashing. The product is used as a chemical sensor element (FIG. 5). A chemical sensor element can also be fabricated when the concentration of fine gold particles is changed within a range between $5.6 \times 10^8$ particles/ml and $5.6 \times 10^9$ particles/ml, and the concentration of polystyrene beads is changed within a range between $5.6 \times 10^8$ particles/ml and $5.6 \times 10^9$ particles/ml.

Comparative Example 1

Amino-group-modified polystyrene (manufactured by Sumitomo Bakelite Co., Ltd.) is used as a substrate; and fine gold particles having a diameter of 100 nm (manufactured by BBI) are used as metal-containing particles.

A dispersion of fine gold particles ($5.6 \times 10^9$ particles/ml) is prepared with pure water. A substrate is immersed in the dispersion and allowed to stand for 24 hours to dispose the fine particles on the substrate. After disposing, the substrate is cleaned with pure water, and dried by blowing nitrogen. In this case, the aggregation of fine gold particles with each other occurred in about half of the chemical sensor elements. The detection sensitivity of the chemical sensor element wherein fine gold particles are aggregated is significantly reduced. The aggregation of fine gold particles can be checked by visually observing a change in color and observing using an optical microscope or SEM.

Example 3

Using chemical sensor elements fabricated in Example 1, Example 2 and Comparative Example 1, target substances present in liquid specimens can be detected as follows:

A method for fixing anti-AFP (α-fetoprotein) antibodies on the surface of gold, which are target-capturing substances used in Example 3, to impart the surfaces of fine gold particles with a capturing capacity is described below. The element is immersed in an ethanol solution of 11-mercaptoundecanoic acid, which has a thiol group with a high affinity for gold, which is a material of the metal-containing particles in the Example 3, to modify the surface of the above-described structure. Thereby, carboxyl groups are exposed on the surface of the structure. In this state, elements are similarly immersed in an aqueous solution of N-hydroxysulfosuccinimide (manufactured by Dojindo Laboratories) and an aqueous solution of 1-ethyl-3-[3-dimethylaminopropyl]carbodiimide hydrochloride (manufactured by Dojindo Laboratories). Thereby, succinimide groups are exposed on the surface of the structure. Furthermore, by bonding streptavidine, the gold surface is modified by streptavidine. Boitinated anti-AFP antibodies are fixed to the streptavidine.

The AFP concentration in a specimen can be specifically measured by the following operations:

(1) Bring the specimen containing AFP, which is a target substance, into contact with the chemical sensor element to capture the AFP on fine gold particles;

(2) Remove the specimen, and clean the fine gold particles using a phosphoric acid buffer solution; and (3) Finally, bring the phosphoric acid buffer solution into contact with the fine gold particles, and measure the absorption spectra of the fine gold particles.

Figure 6:
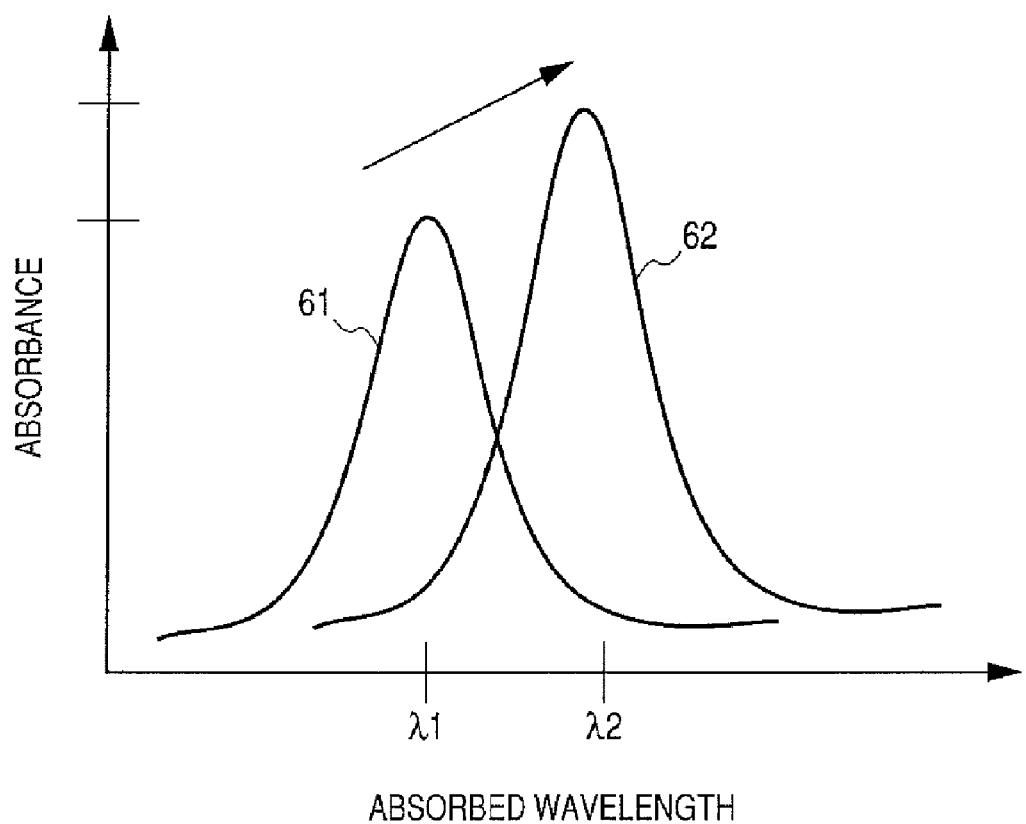
FIG. 6 is a graph illustrating change in detection spectra (absorption spectra) of Example 3.

When the absorption spectra before the reaction are compared with the absorption spectra after the reaction, as, for example, shown in FIG. 6 wherein numeral 61 denotes a spectrum before the reaction, numeral 62 denotes a spectrum after the reaction, and symbols $\lambda_1$ and $\lambda_2$ denote absorbed wavelengths at which spectrums 61 and 62 peak, respectively, the target substance is bonded to the surface of the chemical sensor element by a specific antigen-antibody reaction, and the absorption spectra are shifted. Here, the correlation between the peak strength of the absorption spectra or the shift of the peak wavelength and the AFP concentration have been previously obtained using a known AFP control solution, and the concentration of a trace of AFP in a specimen of an unknown concentration can be obtained.

Although the AFP concentration can be obtained by chemical sensor elements of Examples 1 and 2, the AFP concentration cannot be obtained by chemical sensor elements of Comparative Example 3 in which fine gold particles are aggregated.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A method for fabricating a chemical sensor element in which metal-containing particles are fixed on a substrate, the method comprising the steps of:

preparing a dispersion comprised of metal-containing particles and dielectric particles as dispersoids;

contacting the dispersion with the substrate to fix the metal-containing particles and the dielectric particles on the substrate;

isolating the metal-containing particles and the dielectric particles fixed on the substrate from the dispersion; and removing the dielectric particles fixed on the substrate.

2. The method according to claim 1, wherein a diameter of the metal-containing particles is from 1 nm to 1000 nm and a diameter of the dielectric particles is from 1 nm to 1000 nm.

3. The method according to claim 1, wherein plasma ashing is used for the removing.

* * * * *